US012600946B2

(12) United States Patent
Lim et al.

(10) Patent No.: US 12,600,946 B2
(45) Date of Patent: Apr. 14, 2026

(54) METHOD FOR INCREASING DENDRITIC CELL MIGRATION ABILITY, AND USE THEREOF

(71) Applicant: CHA UNIVERSITY INDUSTRY-ACADEMIC COOPERATION FOUNDATION, Pocheon-si (KR)

(72) Inventors: Dae Seog Lim, Seongnam-si (KR); Soo-yeoun Park, Hongseong-gun (KR); Jun Ho Lee, Yongin-si (KR); So Yeon Choi, Gangdong-gu (KR); Ji Young Yoo, Goyang-si (KR); Nam Chul Jung, Seongnam-si (KR)

(73) Assignee: CHA UNIVERSITY INDUSTRY-ACADEMIC COOPERATION FOUNDATION, Pocheon-si (KR)

( * ) Notice: Subject to any disclaimer, the term of this patent is extended or adjusted under 35 U.S.C. 154(b) by 991 days.

(21) Appl. No.: 16/977,320

(22) PCT Filed: Jan. 28, 2019

(86) PCT No.: PCT/KR2019/001173
§ 371 (c)(1),
(2) Date: Sep. 1, 2020

(87) PCT Pub. No.: WO2019/212123
PCT Pub. Date: Nov. 7, 2019

(65) Prior Publication Data
US 2021/0054335 A1    Feb. 25, 2021

(30) Foreign Application Priority Data

May 4, 2018    (KR) ........................ 10-2018-0052135

(51) Int. Cl.
*C12N 5/0784* (2010.01)
*A61K 40/19* (2025.01)
*A61K 40/22* (2025.01)
*A61K 40/24* (2025.01)
*A61K 40/41* (2025.01)
*A61K 40/42* (2025.01)

(52) U.S. Cl.
CPC ............ *C12N 5/0639* (2013.01); *A61K 40/19* (2025.01); *A61K 40/22* (2025.01); *A61K 40/24* (2025.01); *A61K 40/416* (2025.01); *A61K 40/42* (2025.01); *A61K 2239/31* (2023.05); *A61K 2239/38* (2023.05); *C12N 2500/44* (2013.01); *C12N 2500/84* (2013.01); *C12N 2501/05* (2013.01); *C12N 2501/052* (2013.01); *C12N 2501/22* (2013.01); *C12N 2501/23* (2013.01); *C12N 2501/73* (2013.01)

(58) Field of Classification Search
None
See application file for complete search history.

(56) References Cited

U.S. PATENT DOCUMENTS

2006/0177420 A1 * 8/2006 Felzmann ............ C12N 5/0639
424/85.2
2012/0164114 A1    6/2012 Abbot et al.

FOREIGN PATENT DOCUMENTS

| CN | 104312973 B | 4/2017 |
| KR | 10-1083404 B1 | 11/2011 |
| KR | 10-1117186 B1 | 3/2012 |
| KR | 10-1613675 B1 | 4/2016 |
| KR | 10-1643716 B1 | 7/2016 |
| WO | WO 2012/083021 A1 | 6/2012 |

OTHER PUBLICATIONS

Boullart, 2008, Canc. Immunol. Immunother. vol. 57: 1589-1597.*
Lee, 2021, Biomedicines, pp. 1-14 Progress in Autoimmune Diseases Reserach, 2005, pp. 1-126.*
Efron, 2005, J. Endotoxin Res. vol. 11: 145-160 Carey, 2010, Clin. Breast. Canc. vol. 10: 188-195.*
Song, 2015, PLOS ONE, pp. 1-22.*
MS the disease, 2020, pp. 1-3.*
Umezu-Goto, 2002, J. Cell. Biol. vol. 158: 227-233.*
Li, 2012, Exp. Ther. Med. VOI 4: 131-134.*
Leonhartsberger, 2007, Canc. Immuno. Immunother. VOI. 56: 897-903.*
Lee, 2002, Vaccine, A8-A22.*
"Abstract of DC2018: 15th International Symposium on Dendritic Cells," European Journal of Immunology, Jun. 10-14, 2018, total pp. 193.
Park, S., "Autotaxin Influences of Immunologic Function of Dendritic Cells," CHA University, Department of Biomedical Science, Master's Thesis, Creative Commons, 2018, total pp. 78.
Chen, R. et al., "Lysophosphatidic Acid Modulates the Activation of Human Monocyte-Derived Dendritic Cells," Stem Cells and Development, vol. 15, 2006, pp. 797-804.
Benesch, M.G.K., et al., "Coming of Age for Autotaxin and Lysophosphatidate Signaling: Clinical Applications for Preventing, Detecting and Targeting Tumor-Promoting Inflammation," Cancers, Mar. 15, 2018, vol. 10, No. 73, pp. 1-25.
Panther, E. et al., "The Influence of Lysophosphatidic Acid on the Function of Human Dendritic Cells," The Journal of Immunology, 2002, vol. 169, pp. 4129-4135 (total pp. 8).
Knowlden, S. et al., "The Autotaxin-LPA Axis Emerges as a Novel Regulator of Lymphocyte Homing and Inflammation," The Journal of Immunology, 2014, vol. 192, pp. 851-857 (total pp. 8).

(Continued)

*Primary Examiner* — Amy E Juedes
(74) *Attorney, Agent, or Firm* — Oblon, McClelland, Maier & Neustadt, L.L.P.

(57) ABSTRACT

A method for increasing dendritic cell migration ability, and a use thereof are disclosed. A method according to one aspect can increase the migration ability of mature dendritic cells and increase the induction, by dendritic cells, of inflammatory cytokine production, T lymphocyte proliferation and T lymphocyte polarization, and thus can be used for the prevention or treatment of immune-related diseases.

4 Claims, 16 Drawing Sheets

(56) References Cited

OTHER PUBLICATIONS

Stein, J.V., "T cell mobility as a modulator of interactions with dendritic cells," Frontiers in Immunology, Nov. 2, 2015, vol. 6, Article 559, pp. 1-6 (total pp. 6).

Office Action issued on Mar. 11, 2020 for Korean application No. 10-2018-0052135, 2 pages.

Office Action issued on Sep. 17, 2019 for Korean application No. 10-2018-0052135, 6 pages.

International Search Report issued on Apr. 29, 2019 in PCT/KR2019/001173 filed on Jan. 28, 2019, 3 pages.

* cited by examiner

METHOD FOR INCREASING DENDRITIC CELL MIGRATION ABILITY, AND USE THEREOF

TECHNICAL FIELD

The present application is based on, and claims priority from, Korean Patent Application No. 10-2018-0052135, filed on May 4, 2018, the disclosure of which is hereby incorporated by reference herein in its entirety.

The present disclosure relates to a method of increasing migration ability of dendritic cells, and use thereof.

BACKGROUND ART

Dendritic cells are a type of specialized antigen-presenting cell that mainly perform the function of presenting antigens to T cells, and exist in the form of tree branches in lymph nodes, the spleen, or the thymus, deeper in the skin, or in intercellular spaces of various tissues. Dendritic cells are known to play an important role in T cell activation by absorbing antigens into cells and presenting various antigen samples to T cells along with a major histocompatibility complex (MHC) class I molecule or MHC class II molecule.

In addition, dendritic cells differentiate into different states of maturity depending on the type of environmental signals present in their surroundings, and exist as immature, semi-mature, or mature dendritic cells. Immature dendritic cells are cells found in their initial maturation stage. They perform a primary function of collecting and removing debris from interstitial fluid. However, since immature dendritic cells express low levels of inflammatory cytokines, they are unable to activate T cells even when they encounter T cells. In contrast, mature dendritic cells have the ability to induce an immune response by activating naive T cells.

Recently, dendritic cells have been studied for use as cell therapeutic agents for cancer, immune-related diseases, etc. For example, dendritic cells are able to suppress tumor cells by activating T cells in lymph nodes, and participate in the immune response, and thus may be used to treat infectious diseases, inflammatory diseases, etc. To exhibit these effects, dendritic cells need to migrate to lymph nodes and activate T cells. The migration of dendritic cells to lymph nodes in vivo is very low, at about 2% to about 5% of the number of cells administered.

Accordingly, it is necessary to develop a composition or method capable of improving the migration ability of dendritic cells.

DESCRIPTION OF EMBODIMENTS

Technical Problem

An aspect provides a method of increasing migration ability of dendritic cells.

Another aspect provides a composition including dendritic cells having increased migration ability.

Solution to Problem

An aspect provides a method of preparing mature dendritic cells having increased migration ability, the method including contacting immature dendritic cells with autotaxin.

As used herein, the term "dendritic cell" refers to a professional antigen presenting cell that absorbs an antigen into the cell and processes it to present the antigen or a peptide derived from the antigen, along with a major histocompatibility complex (MHC) class I complex or MHC class II complex. The dendritic cell of the present disclosure refers to a cell having general phenotype and characteristics of dendritic cells, as disclosed in Steinman et al., Annual Rev. Immunol. 9:271-296, 1991 and Banchereau and Steinman Nature 392:245-252, 1998. Dendritic cells include both immunogenic and tolerogenic antigen presenting cells, and are classified into an immature dendritic cell (imDC), a semimature dendritic cell (smDC), and a mature dendritic cell (mDC) depending on maturity.

As used herein, the term "immature dendritic cell" may include imDC, smDC, or a combination thereof. The "imDCs" refer to DCs that perform a primary function of collecting and removing debris from interstitial fluid, but they express low levels of inflammatory cytokines, and therefore, they are unable to activate T cells even when they encounter T cells. The "smDCs" refer to DCs that lost some of the characteristics of immature DCs, but have some of the phenotypic characteristics of mDCs so that they exhibit partially or incompletely matured form and phenotypic characteristics.

The DCs may be obtained from animal's organs, tissues, bone marrow, or blood.

As a medium used in a process of obtaining the DCs, any medium may be used as long as it is generally used for culturing animal cells. Specifically, the medium is a medium containing serum (e.g., fetal bovine serum, equine serum, or human serum). The medium that may be used in the present disclosure may include, for example, RPMI series (e.g., RPMI 1640), Eagles's minimum essential medium (Eagle's MEM, Eagle, H. Science 130:432(1959)), α-MEM (Stanner, C. P. et al., Nat. New Biol. 230:52(1971)), Iscove's MEM (Iscove, N. et al., J. Exp. Med. 147:923(1978)), 199 medium (Morgan et al., Proc. Soc. Exp. Bio. Med. 73:1(1950)), CMRL 1066, RPMI 1640 (Moore et al., J. Amer. Med. Assoc. 199:519(1967)), F12 (Ham, Proc. Natl. Acad. Sci. USA 53:288(1965)), F10 (Ham, R. G. Exp. Cell Res. 29:515(1963)), Dulbecco's modification of Eagle's medium (DMEM, Dulbecco, R. et al., Virology 8:396(1959)), a mixture of DMEM and F12 (Barnes, D. et al., Anal. Biochem. 102:255(1980)), Waymouth's MB752/1 (Waymouth, C. J. Natl. Cancer Inst. 22:1003(1959)), McCoy's 5A (McCoy, T. A., et al., Proc. Soc. Exp. Biol. Med. 100:115 (1959)), and MCDB series (Ham, R. G. et al., In Vitro 14:11(1978)), but is not limited thereto.

In one embodiment of the present disclosure, the imDCs may be obtained by culturing bone marrow cells from which red blood cells were removed, but are not limited thereto.

As used herein, the term "mDC" refers to a cell formed by maturation of an imDC. The mDC has high expression of MHC class II, CD40, CD54, CD80, CD86, and CD274 as well as DC-LAMP; are characterized by release of proinflammatory cytokines, and ability to induce increased proliferation of naive allogeneic T cells and syngeneic T cells and/or increased production of DC cytokines in a mixed lymphocyte reaction. mDCs generally express high levels of CCR7 and CXCR4. mDCs have ability to induce an immune response by activating naive T cells.

As used herein, the term "autotaxin" is a 125-kDa glycoprotein initially isolated from a culture medium of melanoma cells, and also known as ectonucleotide pyrophosphatase/phosphodiesterase family member 2 (ENPP2). Autotaxin has lysophospholipase D activity, and is an extracellular enzyme that functions to generate lysophosphatidic acid (LPA) from lysophosphatidylcholine (LPC).

The autotaxin may be produced according to a known method of producing recombinant proteins, isolated from a living body, or commercially obtained.

The autotaxin includes a functional equivalent thereof. The "functional equivalent" refers to a protein having, as a result of addition, substitution, or deletion of an amino acid, at least 70% or more, specifically 80% or more, more specifically 90% or more, and even more specifically 95% or more sequence homology with an amino acid sequence of the autotaxin protein, and it refers to a protein exhibiting substantially identical physiological activity to the autotaxin protein. As long as the autotaxin protein is involved in the migration ability of DCs, any combination of deletion, insertion, and substitution in a final structure of the protein is also possible.

As used herein, the term "contacting" refers to a state in which autotaxin affects imDCs under sufficient time and conditions. Specifically, the contacting of imDCs with autotaxin may be performed in an RPMI medium, and more specifically, may include culturing the imDCs and autotaxin in the RPMI medium.

The medium may further include components which may be generally included in a cell culture medium, or components which may induce maturation of imDCs, for example, fetal bovine serum (FBS), granulocyte-macrophage colony-stimulating factor (GM-CSF), interleukin (IL), and mercap-toethanol.

The contacting may be performed for about 1 hour to about 48 hours, for about 5 hours to about 40 hours, for about 10 hours to about 35 hours, for about 15 hours to about 30 hours, or for about 20 hours to about 25 hours, specifically for about 24 hours, but is not limited thereto. When the contacting time is too short, maturation of imDCs may not be sufficiently achieved, and when the contacting time is too long, death of DCs may be increased.

The contacting may be performed on about the $4^{th}$ day to about the $8^{th}$ day, on about the $5^{th}$ day to about the $7^{th}$ day, or on about the $6^{th}$ day of imDCs culture.

The method of preparing mDCs having increased migration ability may further include contacting the imDCs with lipopolysaccharide (LPS), keyhole limpet hemocyanin (KLH), or a combination thereof.

The LPS is used as an accelerator that stimulates maturation of imDCs by contacting with imDCs.

The KLH is used to provide information about antigens for DCs which are antigen-presenting cells.

The contacting with LPS, KLH, or a combination thereof may be performed simultaneously with, before, or after contacting the imDCs with autotaxin.

In the method, a concentration of autotaxin may be selected in an appropriate range by those skilled in the art, for example, about 0.01 µg/ml to about 1 mg/ml, about 0.05 µg/ml to about 500 µg/ml, about 0.1 µg/ml to about 100 µg/ml, about 0.5 µg/ml to about 50 µg/ml, about 1 µg/ml to about 30 µg/ml, about 3 µg/ml to about 20 µg/ml, or about 5 µg/ml to about 15 µg/ml.

As used herein, the term "migration ability" may refer to ability of mDCs to migrate. After mDCs capture antigens, they migrate through a lymphatic vessel to lymph nodes where naive T cells exist. These T cells recognize the antigens to induce an immune response. Therefore, it is important to increase the migration ability, which is the ability of mDCs to migrate to lymph nodes, in order to maximize the effect of inducing an immune response.

mDCs prepared by the method has increased migration ability. As compared with general mDCs having no increased migration ability, mDCs having increased migration ability exhibit an increased migration rate to lymph nodes, and therefore, the effect of inducing an immune response in lymph nodes is significantly increased, thereby improving prophylactic or therapeutic effects on autoimmune diseases, cancer, infectious diseases or inflammatory diseases when administered.

In the method, the increased migration ability of mDCS may be attributed to pp38, pJNK, or ERK1/2 signaling.

The method may increase inflammatory cytokine production induction of mDCS. In one embodiment of the present disclosure, it was confirmed that mDCs according to the method have increased ability to induce production of IL-1β, IL-6, IL-12, and TNF-α which are inflammatory cytokines, as compared with mDCs. mDCs may increase expression of the inflammatory cytokines to increase T cell activation.

The method may increase T lymphocyte proliferation induction of mDCs. In one embodiment of the present disclosure, it was confirmed that mDCs according to the method have increased ability to induce T lymphocyte proliferation, as compared with control mDCs.

The method may increase T lymphocyte polarization induction of mDCs. In one embodiment of the present disclosure, it was confirmed that mDCs according to the method have increased ability to induce T lymphocyte polarization, as compared with control mDCs.

mDCs according to the method may have prophylactic or therapeutic effects on a variety of immune-related diseases by inducing inflammatory cytokine production, T lymphocyte proliferation, or T lymphocyte polarization.

Another aspect provides mDCs having increased migration ability, which are prepared by the method.

Still another aspect provides a pharmaceutical composition for preventing or treating a disease selected from the group consisting of autoimmune diseases, cancers, infectious diseases, and inflammatory diseases, the pharmaceutical composition including mDCs having increased migration ability, which are prepared by the method.

Still another aspect provides use of mDCs prepared by the method of culturing mDCs having increased migration ability in preparing a pharmaceutical composition or agent for preventing or treating a disease selected from the group consisting of autoimmune diseases, cancers, infectious diseases, and inflammatory diseases.

Still another aspect provides a method of culturing mDCs having increased migration ability which are used in preparing a medicament for preventing or treating a disease selected from the group consisting of diseases, for example, autoimmune diseases, cancers, infectious diseases, and inflammatory diseases, or use of the mDCs which are prepared by the method of increasing migration ability of mDCs. The method, migration ability, and mDCs having increased migration ability are the same as described above.

The autoimmune diseases include all diseases or disorders caused by an autoimmune reaction in vivo. For example, the autoimmune diseases may include type 1 diabetes, rheumatoid arthritis, multiple sclerosis, systemic lupus erythematosus, Sjogren's syndrome, scleroderma, multiple myositis, chronic active hepatitis, mixed connective tissue disease, primary biliary cirrhosis, malignant anemia, autoimmune thyroiditis, idiopathic addison's disease, Vitiligo, gluten sensitive enteropathy, Graves' disease, myasthenia gravis, autoimmune neutropenia, idiopathic thrombocytopenic purpura, cirrhosis, pemphigus vulgaris, autoimmune infertility, Goodpasture's syndrome, bullous pemphigoid, discoid lupus erythematosus, ulcerative colitis, dense deposit disease, etc.

The cancers may include gastric cancer, lung cancer, breast cancer, ovarian cancer, liver cancer, bronchial cancer, nasopharyngeal cancer, laryngeal cancer, pancreatic cancer, bladder cancer, colon cancer, cervical cancer, brain cancer, prostate cancer, bone cancer, skin cancer, thyroid cancer, parathyroid cancer, ureteral cancer, etc., but are not limited thereto.

The inflammatory diseases collectively refer to diseases in which inflammation is a main lesion, and may include any one selected from the group consisting of edema, allergy, asthma, conjunctivitis, periodontitis, rhinitis, otitis media, sore throat, tonsillitis, pneumonia, gastric ulcer, gastritis, Crohn's disease, colitis, hemorrhoids, gout, ankylosing spondylitis, rheumatic fever, lupus, fibromyalgia, psoriatic arthritis, osteoarthritis, rheumatoid arthritis, periarthritis of shoulder, tendonitis, tendosynovitis, myositis, hepatitis, cystitis, nephritis, Sjogren's syndrome, and multiple sclerosis, but are not limited thereto.

The infectious diseases collectively refer to diseases caused by infection with pathogens such as viruses, bacteria, fungi, and parasites, and may include human immunodeficiency virus (HIV), hepatitis B virus or hepatitis C virus (HBV or HCV), Epstein-Barr virus (EBV), cytomegalovirus (CMV), enterovirus, influenza with Influenza virus A, B, and C, syncytial respiratory virus (SRV), or HTLV, bacteria and/or toxin thereof (tetanus, diphtheria, pneumococci, meningococci, staphylococci containing methicillin resistant forms, Klebsiellas, Shigellas, *Pseudomonas aeruginosa*, enterobacteria or antibiotic resistant pathologies containing nosocomial diseases), parasites (paludisme, leishmaniasis, trypanosomiasis), and chikungunya, avian influenza, severe acute respiratory syndrome virus (SARS), Ebola virus, emerging diseases such as hemorrhagic fever-related virus such as Dengue fever virus or West Nile virus, Anthrax, botulism, Plague, smallpox, and poxvirus, Tularaemia, haemorrhagic fever agents, brucellosis, *Staphylococcus* B Enterotoxins, diphtheric toxin, or bioterrorism-related diseases such as viral Encephalitis, but are not limited thereto.

The composition has effects of preventing or treating diseases, for example, cancers, autoimmune diseases, infectious diseases, or inflammatory diseases, in which mDCs with increased migration ability activate T cells in lymph nodes and induce an immune response.

As used herein, the term "preventing" means all of actions by which occurrence of autoimmune diseases, cancers, infectious diseases, or inflammatory diseases is restrained or retarded by administering the composition.

As used herein, the term "treating" means all of actions by which autoimmune diseases, cancers, infectious diseases, or inflammatory diseases have taken a turn for the better or been modified favorably by administering the composition.

A pharmaceutically acceptable carrier included in the composition may be those commonly used in formulation, including lactose, dextrose, sucrose, sorbitol, mannitol, starch, acacia rubber, calcium phosphate, arginate, gelatin, calcium silicate, microcrystalline cellulose, polyvinylpyrrolidone, cellulose, water, syrups, methyl cellulose, methyl hydroxybenzoate, propyl hydroxybenzoate, talc, magnesium stearate, mineral oils, etc., but is not limited thereto. In addition to the above components, the composition may further include a lubricant, a humectant, a sweetener, a flavoring agent, an emulsifier, a suspending agent, a preservative, etc. Appropriate pharmaceutically acceptable carriers and formulations are described in detail in Remington's Pharmaceutical Sciences (19th ed., 1995).

Appropriate administration dosages of the composition may be variously prescribed by factors, such as a formulation method, mode of administration, a patient's age, weight, sex, disease conditions, foods, administration time, administration route, excretion rate, and reaction responsiveness.

Further, the composition may be used as a cell therapeutic agent.

Further, the composition may be used together with a common immune adjuvant. The immune adjuvant is a substance that non-specifically boosts immune responses to antigens during initial activation of immune cells, and refer to an agent, a molecule, etc. which is not an immunogen to the host, but enhances immunity by increasing activity of cells in the immune system. This adjuvant is reported to act via various mechanisms, including increasing the surface area of an antigen, or prolonging antigen retention in the body to allow the immune system to access the antigen, to delay antigen release, to target the antigen to macrophages, or to activate macrophages, etc. Common immune adjuvants may include Freund's adjuvant, aluminum compounds, muramyl dipeptide, LPS, etc.

The composition may also maximize its effect in combination with radiotherapy or in combination with anticancer agents, after surgery.

Still another aspect provides a method of treating a disease selected from the group consisting of autoimmune diseases, cancers, infectious diseases, and inflammatory diseases, the method including administering, to a subject, a therapeutically or pharmaceutically effective amount of the mDCs prepared by the method of preparing mDCs having increased migration ability.

The term "administering" refers to introducing a predetermined substance into a subject by any suitable method. The substance may be administered via any general route, as long as it is able to reach a target tissue. The administering may be administering via intraperitoneal, intravenous, intramuscular, subcutaneous, intradermal, oral, topical, intranasal, intrapulmonary, or rectal route, but is not limited thereto. The administering may also be performed via any apparatus capable of moving to target cells. The administration dosage may be appropriately selected depending on the type of cancer, the administration route, a patient's age and sex, and disease severity. For adults, about $1 \times 10^6$ cells to about $1 \times 10^{11}$ cells may be administered on average.

The "therapeutically effective amount" means an amount sufficient to exhibit a therapeutic effect when administered to a subject or cell in need of treatment. The "treating" means treating a disease or medical symptoms in a subject, for example, a mammal including a human, and includes: (a) preventing occurrence of a disease or medical symptoms, i.e., prophylactic treatment of a patient; (b) alleviating a disease or medical symptoms, i.e., removing or recovering the disease or medical symptoms in a patient; (c) inhibiting a disease or medical symptoms, i.e., slowing or stopping progression of the disease or medical symptoms in a subject; or (d) relieving a disease or medical symptoms in a subject.

Advantageous Effects of Disclosure

A method according to an aspect may increase migration ability of mature dendritic cells, and may increase induction of inflammatory cytokine production, induction of T lymphocyte proliferation, and induction of T lymphocyte polarization of dendritic cells, and thus may be used in preventing or treating immune-related diseases.

MODE OF DISCLOSURE

Figure 1:
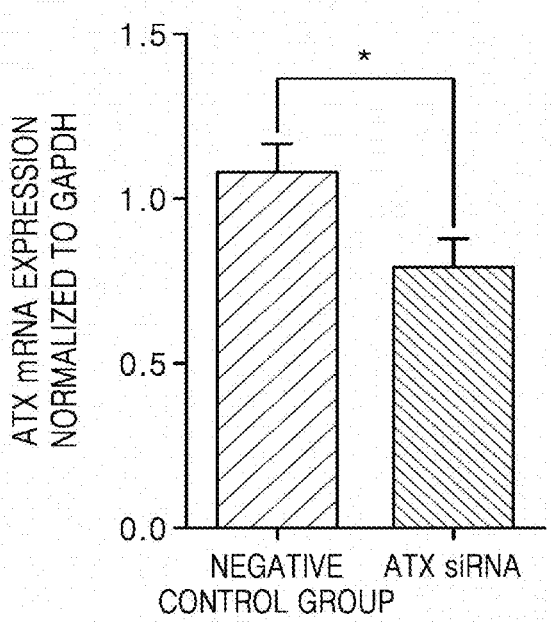
FIG. 1 shows a graph showing RT-PCR results of examining autotaxin gene expression in autotaxin-specific siRNA-treated mature dendritic cells and control dendritic cells (*p<0.05)

Hereinafter, the present disclosure will be described in more detail with reference to exemplary embodiments. However, these exemplary embodiments are only for illustrating the present disclosure, and the scope of the present disclosure is not limited thereto.

Example 1: Examination of Effects of Autotaxin Gene on Characteristics of Mature Dendritic Cells Effects of autotaxin gene on characteristics of mature dendritic cells were examined by the following experiments.
1.1 Suppression of Autotaxin Gene Expression Level in Mature Dendritic Cells by Autotaxin-Specific siRNA Autotaxin gene expression levels in mature dendritic cells were suppressed by using autotaxin-specific siRNA. In detail, siRNA (Bioneer, Daejeon, Korea) targeting mouse Enpp2 mRNA was introduced into cells at a concentration of 100 nM using a lipofectamine 3000 (Invitrogen, CA, USA) system. On the $6^{th}$ day after dendritic cell culture, all cells were collected and suspended in a basic dendritic cell medium containing 5% fetal bovine serum, and dispensed at a density of $2 \times 10^5$ cells/well in a 6-well culture plate. 4 hr after siRNA transfection, maturation of siRNA-treated dendritic cells was induced for 24 hr by replacing the medium with a dendritic cell culture medium containing LPS, and a fresh dendritic cell culture medium was replaced for an immature dendritic cell group. Here, scramble siRNA (Bioneer) was used as a negative control group, and the experiment was repeated in triplicate. Information about siRNA targeting Enpp2 mRNA is shown in Table 1.

TABLE 1

| siRNA | Sequence |
|---|---|
| Enpp2 siRNA-1 | 5'-GGG UCU UGG UGA AGA AAU AdTdT-3' |
| Enpp2 siRNA-2 | 5'-UAU UUC ACC AAG ACC CdTdT-3' |

Expression of autotaxin gene and protein in autotaxin-specific siRNA-treated mature dendritic cells and the negative control group was examined by qRT-PCR and Western blotting, respectively. For qRT-PCR, a labozol reagent (Cosmo genetech, Seoul, Korea) was used to isolate RNA from dendritic cells. cDNA was synthesized from the isolated RNA using a cDNA synthesis kit (Cosmo genetech). A SensiFAST™ SYBR No-ROX kit (Bioline, Sydney, Australia) was used in quantitative real-time PCR of Enpp2 gene. Reaction conditions are as follows: a reaction at 95° C. for 10 min; 35 cycles of reactions at 94° C. for 20 sec, at 62° C. for 30 sec, and at 72° C. for 20 sec; and a final reaction at 72° C. for 5 min. Gene expression levels were analyzed by normalizing a threshold cycle (Ct) value of each gene to a Ct value of GAPDH, and then by comparing changes of the Ct values.

For Western blotting, dendritic cells were suspended in an RPMI 1640 medium supplemented with 2% fetal bovine serum, and then dispensed at a density of $1 \times 10^6$ cells/well in a 6-well plate, and cultured under conditions of 37° C. and 5% $CO_2$ for 24 hr. 24 hr later, the cell culture medium was collected and concentrated by centrifugation at 3000 g for 20 min using an Amicon Ultra-2 Centrifugal Filter Unit with Ultracel-10 membrane (Millipore, Germany). Intracellular proteins of dendritic cells were extracted using PRO-PREP™ (iNtRON Biotechnology, Gyeonggi, Korea) and a phosphatase inhibitor cocktail (Calbiochem, CA, USA). Protein concentrations were determined by a Bradford (Thermo, MA, USA) assay. The quantified proteins were separated on SDS-PAGE, and the separated proteins were adsorbed onto a PVDF membrane (Biorad, CA, USA). The PVDF membrane was blocked with 5% skim milk in PBST at room temperature for 1 hr, and treated with a 1:2000 dilution of a primary antibody with 5% skim milk, and then allowed to react at 4° C. for 18 hr. Thereafter, the membrane was washed with 1×PBST for 10 min three times, and then treated with a secondary antibody at 1:5000, and then allowed to react at room temperature for 2 hr. The membrane was washed again with 1×PBST three times, and then exposed to an ECL solution (Thermo) to visualize protein bands using LAS-4000 (Fuji film, Tokyo, Japan). Results were analyzed using a Multi Gauge software V3.0 (Fuji film).

FIG. 1 shows a graph showing RT-PCR results of examining autotaxin gene expression in autotaxin-specific siRNA-treated mature dendritic cells and control dendritic cells (*p<0.05).

Figure 2:
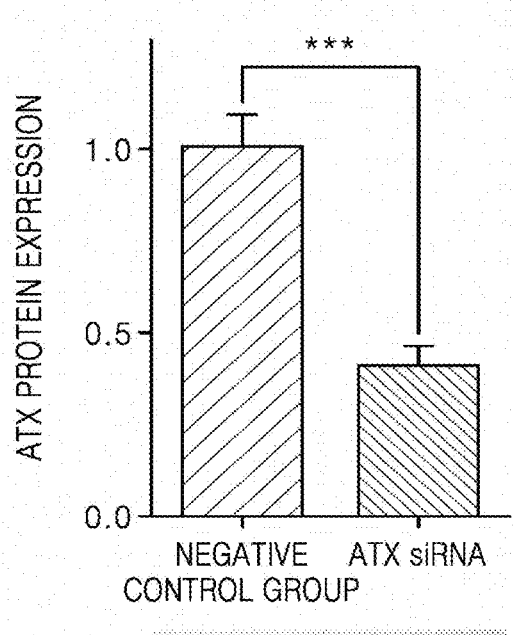
FIG. 2 shows a graph showing Western blotting results of examining autotaxin protein expression in autotaxin-specific siRNA-treated mature dendritic cells and control dendritic cells (***p<0.001)

FIG. 2 shows a graph showing Western blotting results of examining autotaxin protein expression in autotaxin-specific siRNA-treated mature dendritic cells and control dendritic cells (***p<0.001).

As shown in FIGS. 1 and 2, 25% or more reduction in autotaxin (ATX) mRNA and protein expression was observed in autotaxin-specific siRNA-treated mature dendritic cells.

1.2 Examination of Changes in Surface Phenotype Expression in Mature Dendritic Cells According to Suppression of Autotaxin Gene Expression To examine a relationship between the autotaxin gene expression and surface phenotype expression, flow cytometry was performed as follows. $2 \times 10^5$ cells to $5 \times 10^5$ cells were washed with PBS (Lonza), and then stained with fluorescence-labeled monoclonal antibodies. The used monoclonal antibodies for flow cytometry are shown in Table 2 below. To examine cell viability, propidium iodide (PI) staining was performed. For staining of cytokines in T cells, cells were treated with GolgiStop (BD Bioscience, CA, USA) for 4 hr. 4 hr later, T cells were collected and CD4 was stained, and then put and fixed in a fixation/permeabilization solution (BD) at room temperature for 30 min. After washing with FACS buffer, staining was performed using IFN-γ and IL-17A monoclonal antibodies for 30 min. Fluorescence-labeled cells were washed with FACS buffer, and then detected using a FACS Calibur (BD). All data were analyzed using FlowJo (Tree Star, CA, USA).

TABLE 2

| Specificity | Clone | Conjugates | Supplier |
|---|---|---|---|
| CD11c | N418 | PE | eBioscience |
| CD14 | Sa14-2 | FITC | Biolegend |
| CD40 | 3/23 | PE | BD |
| CD54 | 3E2 | FITC | BD |
| CD80 | 16-10A1 | PE | eBioscience |
| CD86 | PO3 | FITC | Biolegend |
| H-2Db | KH95 | FITC | Biolegend |
| I-A$^b$ | AF6-120.1 | PE | BD |
| CD4 | RM4-5 | APC | Biolegend |
| IFN-γ | XMG1.2 | FITC | Biolegend |
| IL-17A | TC11-18H10 | PE | BD |

FIG. 3 shows histograms (A) and fluorescence intensity (B), each showing expression of surface antigens CD11c, CD14, CD40, CD54, CD80, CD86, MHCI, and MHCII in mature dendritic cells (ATX siRNA), in which autotaxin expression was suppressed by autotaxin-specific siRNA, a negative control group, and mature dendritic cells (mDCs).

Figure 3A:
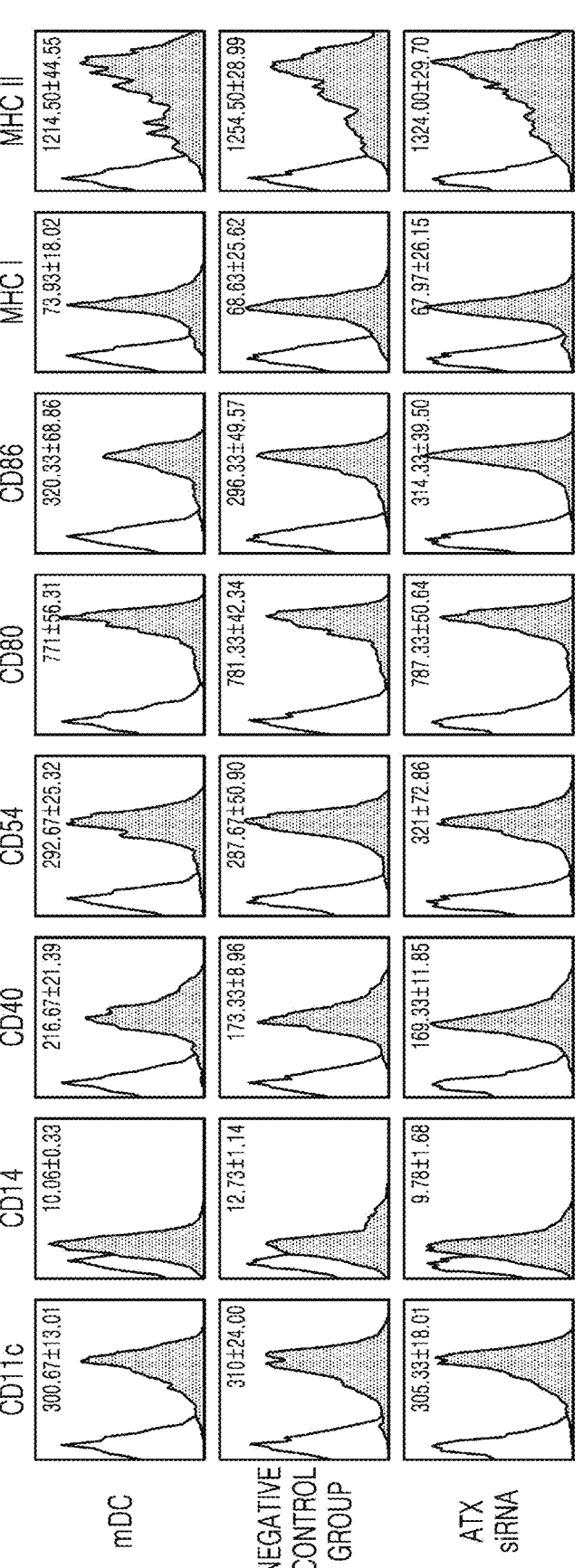
FIG. 3A shows histograms showing expression of the surface antigens CD11c, CD14, CD40, CD54, CD80, CD86, MHCI, and MHCII in mature dendritic cells (ATX siRNA), in which autotaxin expression was suppressed by autotaxin-specific siRNA, a negative control group, and mature dendritic cells (mDCs)
Figure 3B:
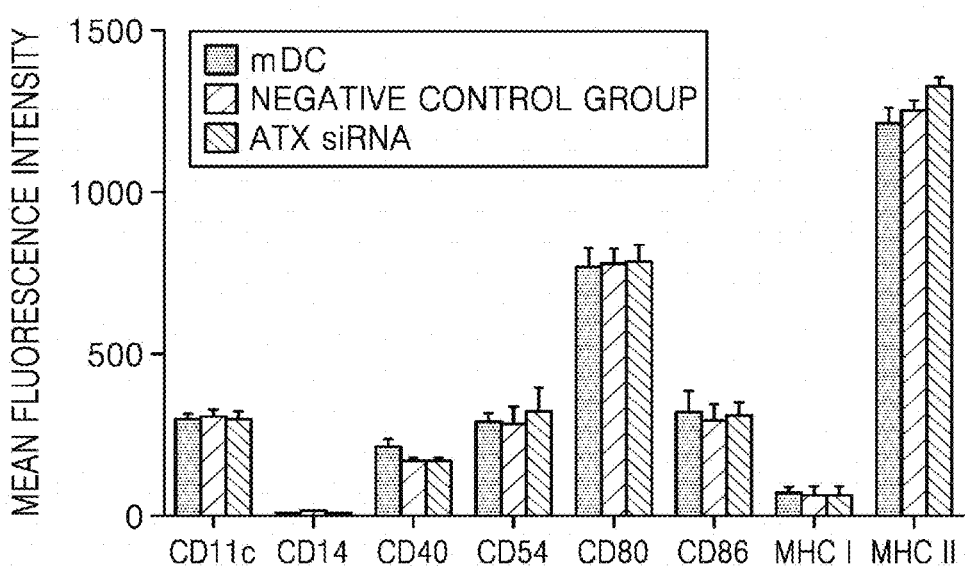
FIG. 3B shows fluorescence intensity showing expression of the surface antigens CD11c, CD14, CD40, CD54, CD80, CD86, MHCI, and MHCII in mDCs (ATX siRNA), in which autotaxin expression was suppressed by autotaxin-specific siRNA, a negative control group, and mDCs.

As shown in FIGS. 3A and 3B, a similar surface antigen expression was observed in each of the mDCs. In detail, it was confirmed that CD14 which is a monocyte surface antigen was rarely expressed, and CD11c which is a representative surface antigen of dendritic cells was highly expressed. Further, it was confirmed that CD40 which is a T lymphocyte stimulatory molecule, CD54 which is a T lymphocyte adhesion molecule, and CD80 and CD86 which are costimulatory molecules, were highly expressed.

Accordingly, it was confirmed that changes in the autotaxin gene expression do not affect surface phenotype expression of mDCs.

1.3 Examination of Changes in Cytokine Expression in mDCs According to Suppression of Autotaxin Gene Expression To examine a relationship between the autotaxin gene expression and cytokines secreted by mDCs, cytokine concentrations in culture media of mDCs were measured using ELISA as follows.

Splenocytes isolated from C57BL/6 mouse were suspended in an RPMI 1640 containing 10% fetal bovine serum, and passed through a nylon wool column to isolate CD3+ T lymphocytes. $2 \times 10^5$ mDCs and $2 \times 10^6$ T lymphocytes were co-cultured in a 6-well pate for 3 days. Cytokine concentrations in the co-culture medium were analyzed using mouse interleukin-1β (IL-1β), IL-6, tumor necrosis factor-α (TNF-α) (Biolegend, CA, USA), and IL-12p70 (BD Bioscience) ELISA kit. Results are expressed as mean±SEM.

Figure 4:
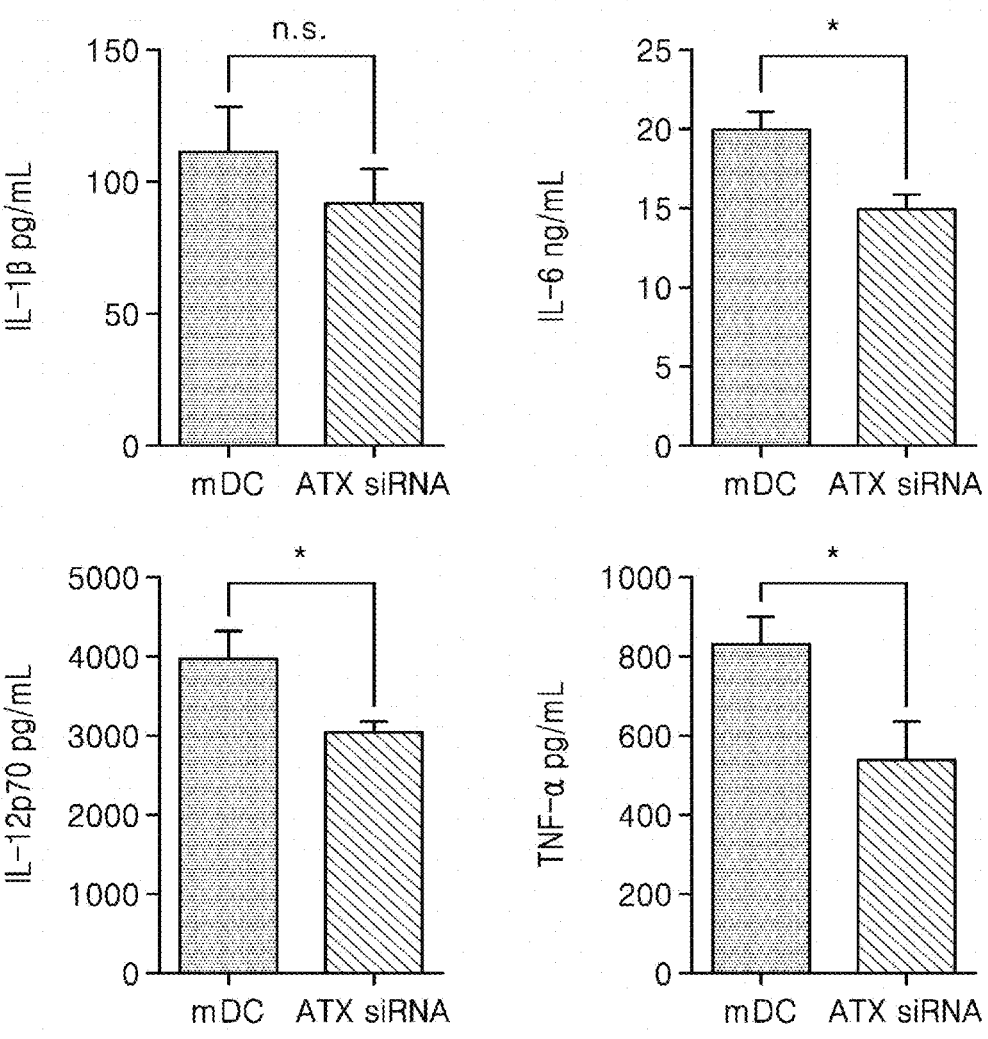
FIG. 4 shows a graph showing ELISA results of examining inflammatory cytokine concentrations in a co-culture medium of mDCs (ATX siRNA), in which autotaxin expression was suppressed by autotaxin-specific siRNA, and mDCs with T lymphocytes (*p<0.05)

FIG. 4 shows a graph showing ELISA results of examining inflammatory cytokine concentrations in the co-culture medium of mDCs (ATX siRNA), in which autotaxin expression was suppressed by autotaxin-specific siRNA (ATX siRNA), and mDCs with T lymphocytes (*p<0.05).

As shown in FIG. 4, the concentrations of inflammatory cytokines in the cell culture medium of the autotaxin expression-suppressed mDCs were about 15% lower than those in the cell culture medium of the control mDCs.

Accordingly, concentrations of TNF-α which is an inflammatory cytokine representing innate immunity, IL-12 which is a cytokine inducing Th1 immune response, and IL-1β and IL-6 which are representative inflammatory cytokines, were reduced, indicating that immune and inflammatory responses of autotaxin expression-suppressed mDCs were reduced.

1.4 Examination of Changes in T Lymphocyte Proliferation Ability of mDCs According to Suppression of Autotaxin Gene Expression To examine a relationship between the autotaxin gene expression and T lymphocyte proliferation ability of mDCs, mDCs and CD3+ T cells were co-cultured at a ratio of 1:10 for 72 hr. CD3+ cells were isolated from splenocytes of naive C57BL/6 mouse, and stained with carboxyfluorescein succinmidyl ester (CFSE) at a final concentration of 4 μM. CFSE-labeled cells were washed, and counted, and then co-cultured with dendritic cells.

Figure 5:
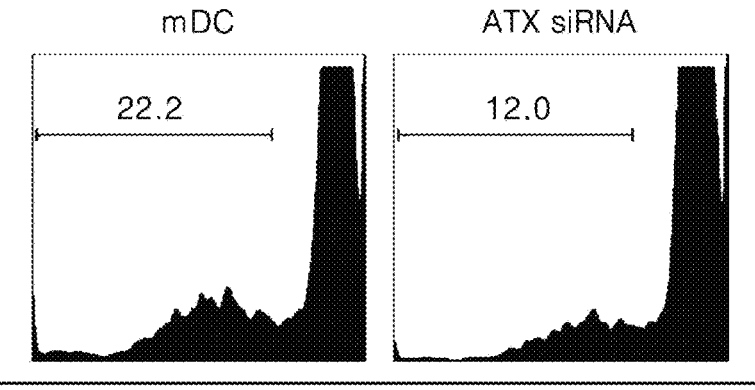
FIG. 5 shows experimental results of examining T cell proliferation ability in autotaxin gene expression-suppressed mDCs (ATX siRNA) and mDCs.

FIG. 5 shows experimental results of examining T cell proliferation ability in autotaxin gene expression-suppressed mDCs (ATX siRNA) and mDCs.

As shown in FIG. 5, the autotaxin gene expression-suppressed mDCs showed about 45% lower T lymphocyte proliferation ability than the normal mDCs. Accordingly, it was confirmed that suppression of autotaxin gene expression inhibits T lymphocyte proliferation ability in mDCs.

1.5 Examination of mDC-Mediated T Lymphocyte Polarization According to Suppression of Autotaxin Gene Expression To examine correlation between the suppression of autotaxin gene expression and mDC-mediated T lymphocyte polarization, the following experiment was performed.

mDCs and CD3+ T cells were co-cultured at a ratio of 1:10 for 72 hr. The cells were stained with anti-CD4 and anti-IFN-γ antibodies, or anti-IL-17A antibody, followed by flow cytometry.

Figure 6:
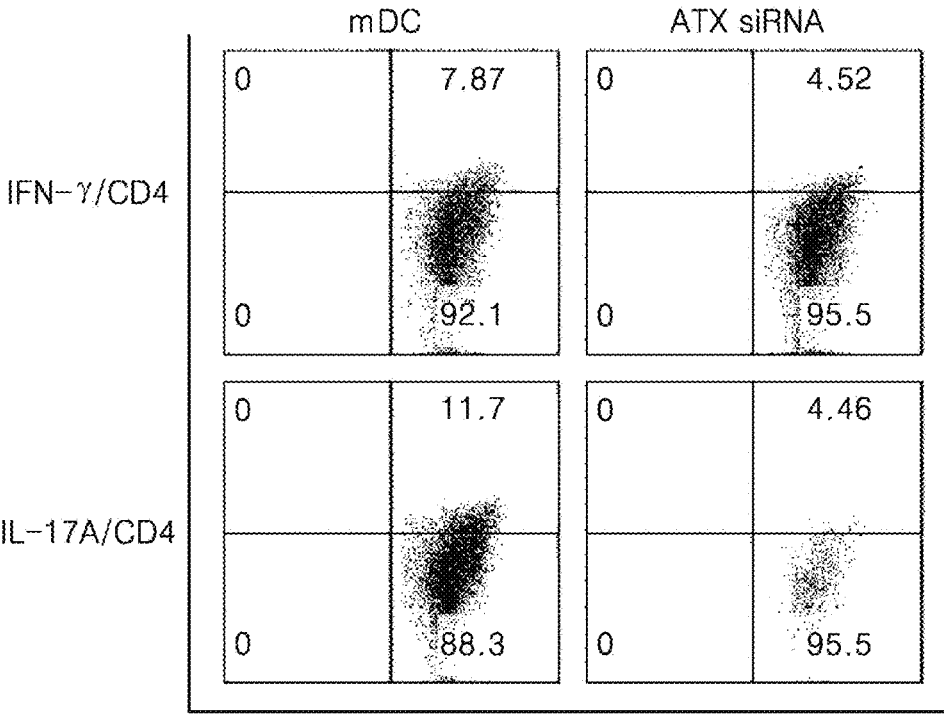
FIG. 6 shows flow cytometry results of examining IFN-γ/CD4 and IL-17/CD4 in autotaxin gene expression-suppressed mDCs (ATX siRNA) and normal mDCs.

FIG. 6 shows flow cytometry results of examining IFN-γ/CD4 and IL-17/CD4 in autotaxin gene expression-suppressed mDCs (ATX siRNA) and normal mDCs.

As shown in FIG. 6, about 50% low differentiation of T cells into Th1 and Th17 subtype cells was observed, when co-cultured with autotaxin gene expression-suppressed mDCs, as compared with mDCs.

Further, each of mDCs and CD3+ T cells were co-cultured at a ratio of 1:10 for 72 hr, and a cell culture supernatant was harvested. Expression of cytokines (IFN-γ, IL-17A, IL-4, IL-10) was examined by ELISA. Data were expressed as mean±SEM (n=3).

Figure 7:
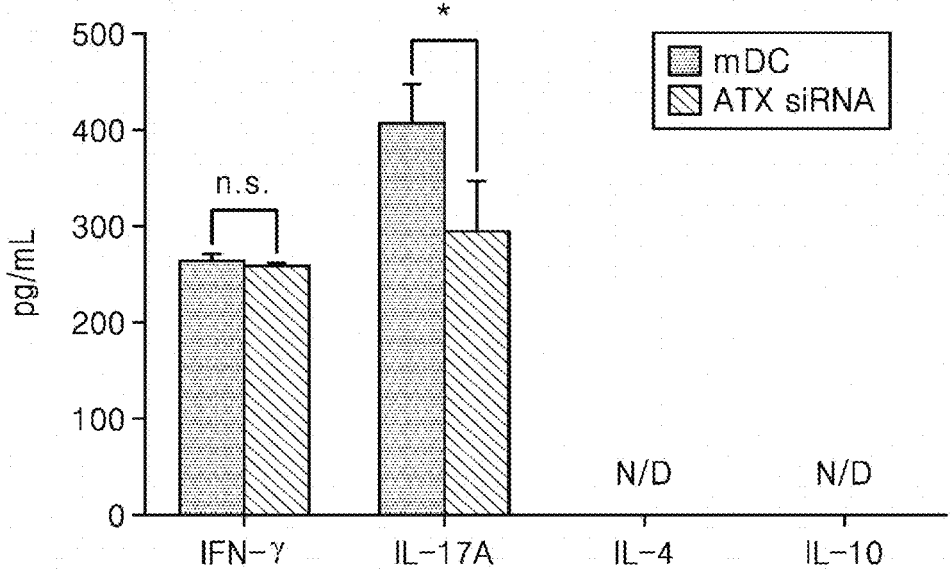
FIG. 7 shows a graph showing ELISA results of examining cytokine concentrations in a co-culture medium of autotaxin gene expression-suppressed mDCs (ATX siRNA) and mDCs with CD3+ T cells.

FIG. 7 shows a graph showing ELISA results of examining cytokine concentrations in a co-culture medium of autotaxin gene expression-suppressed mDCs (ATX siRNA) and mDCs with CD3+ T cells.

As shown in FIG. 7, low IFN-γ and IL-17 concentrations in the co-culture medium were observed in the autotaxin gene expression-suppressed mDCs.

1.6 Examination of Change in Rho A Protein Expression According to Treatment with Autotaxin Enzyme Activity Inhibitor The autotaxin gene expression of mDCs was suppressed by treatment with autotaxin-specific siRNA. However, since autotaxin is released and present in the cell culture medium, HA 130 (Albers, Dong et al. 2010) and PF8380 (Gierse, Thorarensen et al. 2010) which are substances capable of inhibiting autotaxin enzyme activity were added to mDCs during culture, followed by culture for 7 days.

Figure 8:
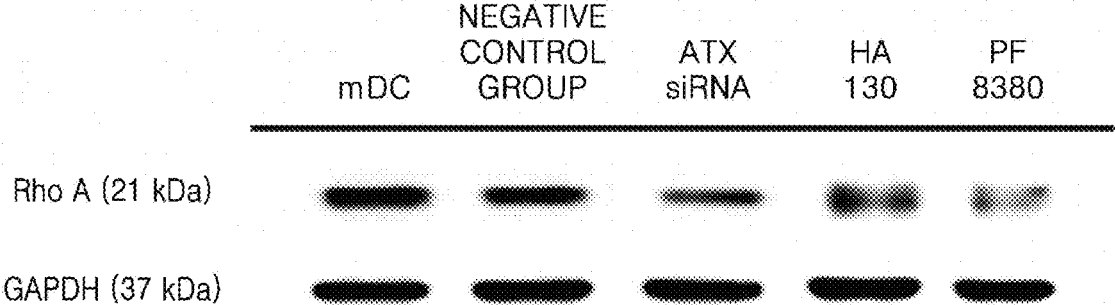
FIG. 8 shows Western blotting results of examining Rho A protein.

After addition, Rho A protein which is known to be involved in cell migration in the downstream signal transduction of LPA receptor of which ligand is LPA as a product of autotaxin enzyme was examined by Western blotting, and results are shown in FIG. 8.

As shown in FIG. 8, when autotaxin-suppressed DCs (ATX siRNA) were treated with HA 130 and PF8380, Rho A protein expression was reduced by about 45% or more, as compared with mDCs.

1.7 Examination of In Vitro Migration Ability of mDCs According to Suppression of Autotaxin Gene Expression To examine in vitro migration ability of mDCs according to suppression of autotaxin gene expression, a migration assay was performed as follows.

A transwell plate with 8.0 μm pore polycarbonate membrane (Corning, NY, USA) was used. mDCs cultured for 7 days were harvested, and then suspended in an RPMI 1640 medium. $5\times10^5$ cells/500 μL thereof was put in the upper portion of the transwell plate, and 500 μL of RPMI 1640 supplemented with 2% fetal bovine serum and 100 ng/mL recombinant mouse CCL19 (R&D systems) was put in the lower portion of the transwell plate. After incubation under conditions of 37° C. and 5% $CO_2$ for 1 hr, the culture medium in the lower portion of the transwell was transferred to a 5-mL round bottom tube, and then the number of cells was counted using a FACS Calibur for 1 min. Measurement results are shown in FIG. 9.

Figure 9:
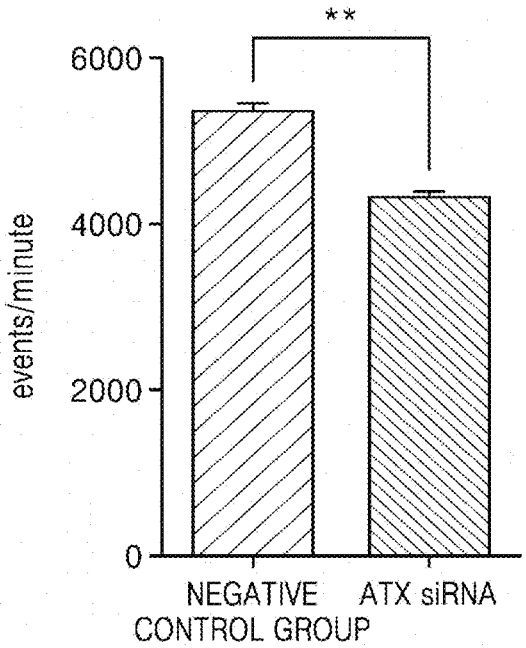
FIG. 9 shows a graph showing migration assay results of examining in vitro migration ability of mDCs according to suppression of autotaxin gene expression.

As shown in FIG. 9, autotaxin expression-suppressed mDCs (ATX siRNA) showed about 20% reduction in the cell migration ability, as compared with mDCs (negative control group).

1.8 Examination of Change in CCR7 Expression According to Suppression of Autotaxin Gene Expression CCR7 which is a homing receptor of DCs is known to be involved in migration of DCs. Therefore, to examine whether CCR7 is associated with the change in the migration ability of mDCs according to suppression of autotaxin gene expression, CCR7 expression in mDCs was examined by qRT-PCR, and results are shown in FIG. 10.

Figure 10:
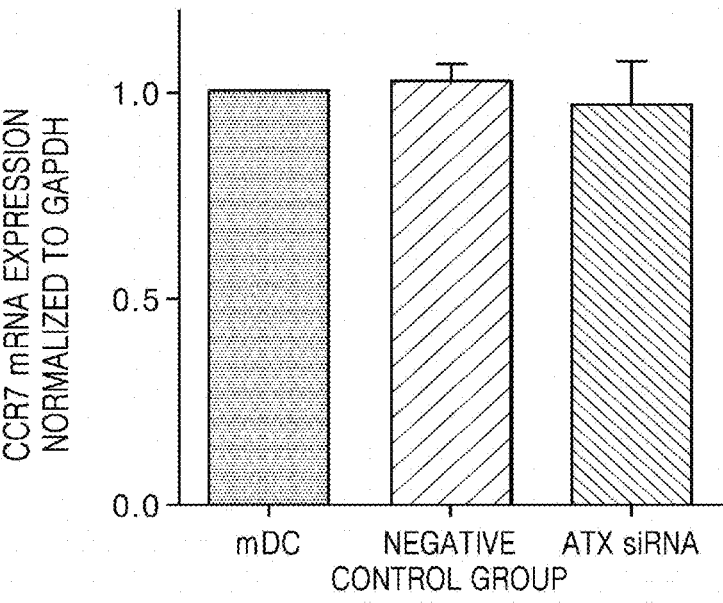
FIG. 10 shows a graph showing qRT-PCR results of examining changes in CCR7 expression in mDCs according to suppression of autotaxin gene expression.

As shown in FIG. 10, it was confirmed that there was little difference in the CCR7 expression levels between the autotaxin expression-suppressed mDCs, negative control group, and mDCs.

Accordingly, it was confirmed that the change in the migration ability according to suppression of autotaxin expression is regulated independently from CCR7 expression.

1.9 Examination of Cause of Cytokine Reduction According to Suppression of Autotaxin Gene Expression In above exemplary embodiment, the reduced cytokine expression by suppression of autotaxin gene expression was observed. Therefore, to examine the cause of the reduced cytokine expression, intracellular signaling proteins (pp38, ERK 1/2, pJNK, and NF-κB) in mDCs were examined by Western blotting.

Figure 11:
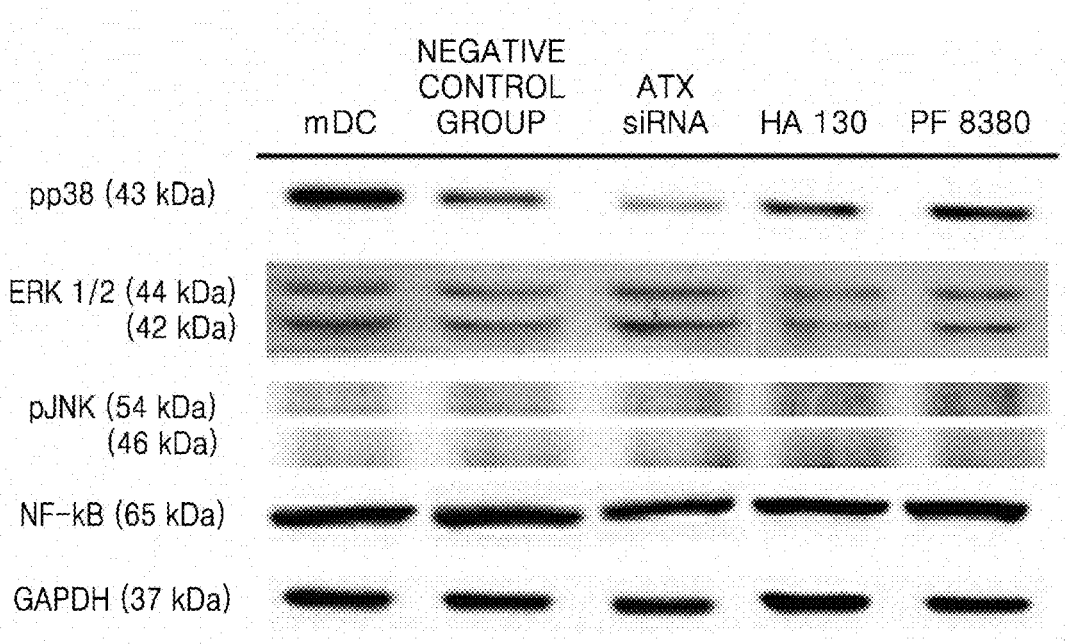
FIG. 11 shows photographs showing Western blotting results of examining pp38, ERK 1/2, pJNK, and NF-κB protein levels in mDCs, a negative control group, mDCs in which autotaxin expression was suppressed by autotaxin-specific siRNA, HA130-treated mDCs, and PF8380-treated mDCs.

FIG. 11 shows photographs showing Western blotting results of examining pp38, ERK 1/2, pJNK, and NF-κB protein levels in mDCs, a negative control group, mDCs in which autotaxin expression was suppressed by autotaxin-specific siRNA, HA130-treated mDCs, and PF8380-treated mDCs.

As shown in FIG. 11, it was confirmed that pp38 and MAPK(ERK 1/2) expression was significantly reduced in autotaxin expression-reduced mDCs, as compared with the control group.

Therefore, it was confirmed that the change in the migration ability of mDCs by the reduced autotaxin expression is associated with the change in pp38 and MAPK expression.

Taken together, the above experimental results showed that the reduced autotaxin expression by siRNA in mDCs deteriorates overall functions of DCs, including reduction of cytokine expression, reduction of T cell proliferation-inducing ability, etc. It was also confirmed that cell migration ability is reduced according to the reduction of autotaxin expression, which is associated with the change in cytokine expression.

Example 2. Preparation of mDCs Having Improved Migration Ability

Example 1 showed that when autotaxin expression was reduced in mDCs, cell migration ability was reduced. Therefore, it was examined whether cell migration ability may be improved by adding the autotaxin protein which is an extracellular enzyme during culture of the DCs.

Animal experiments were conducted according to the Institutional Animal Care and Use Committees (IACUC) of CHA University (IRB number: IACUC170111). To isolate DCs, 6-8-week old male C57BL/6 mice were purchased for use from Orient Bio (Seongnam-si, Korea). Mouse bone marrow cells were obtained from tibia and femur of C57BL/6 mouse by washing bone marrow cavity with RPMI 1640 containing 25 mM HEPES (Lonza, MD, USA). Impurities were removed from the obtained bone marrow cells using a 70 $\mu$m cell strainer, centrifugation was performed at 1600 rpm for 5 min, and then red blood cells were removed using ACK lysis buffer which is a red blood cell lysing agent. The bone marrow cells were suspended in a DC culture medium which is an RPMI 1640 medium supplemented with 10% fetal bovine serum, 100 units/mL penicillin, 100 $\mu$g/mL streptomycin, 2 mM GlutaMax™, 55 nM 2-mercaptoethanol (Gibco, NY, USA), 20 ng/mL recombinant mouse (rm)GM-CSF, 20 ng/mL rmIL-4 (JW CreaGene, Gyeonggi, Korea), and $3\times10^7$ cells were dispensed in a 6-well plate, followed by incubation under conditions of 37° C. and 5% $CO_2$. On the $2^{nd}$ day of culture, non-adherent cells were removed, and the DC culture medium of the same composition was added. On the $4^{th}$ day of culture, half of the culture medium was collected and replaced with a fresh DC culture medium. On the $6^{th}$ day of culture, all cells were collected, and a fresh DC culture medium was replaced for imDCs, and cells to be differentiated into mDCs were suspended in a DC culture medium supplemented with 1 $\mu$g/mL lipopolysaccharide (LPS) and 10 $\mu$g/mL KLH (Sigma Aldrich, MO, USA), and maturation was induced for 24 hr. Here, 10 $\mu$g/mL of the recombinant autotaxin protein (R&D systems, MN, USA) was treated along with LPS stimulation, thereby preparing mDCs having improved migration ability by the above method.

Example 3. Characterization of mDCs Having Improved Migration Ability

3.1 Examination of Surface Phenotype Expression

Figure 12A:
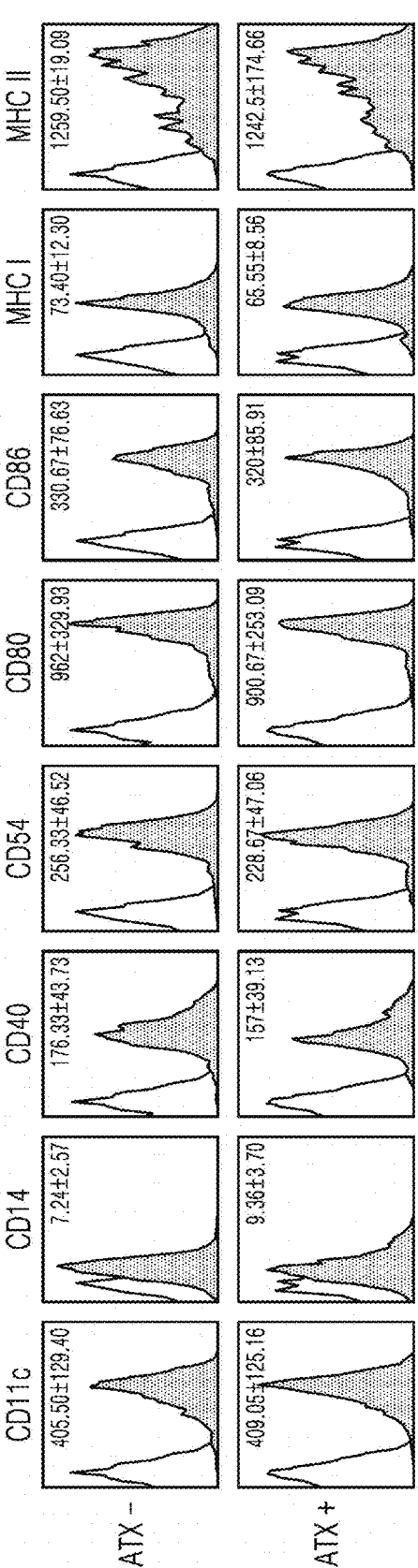
FIG. 12A shows histograms showing flow cytometry results of examining cell surface marker expression in mDCs having improved migration ability, to which a recombinant autotaxin protein has been added during culture, and in mDCs to which no recombinant autotaxin protein has been added during culture.
Figure 12B:
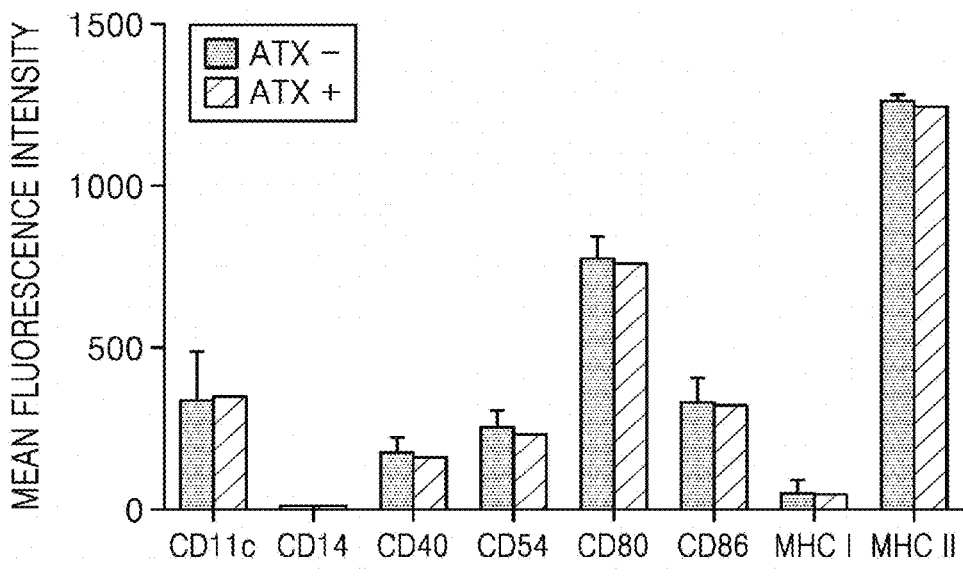
FIG. 12B shows a graph showing quantification of flow cytometry results of examining cell surface marker expression in mDCs having improved migration ability, to which the recombinant autotaxin protein has been added during culture, and in mDCs to which no recombinant autotaxin protein has been added during culture.

Surface marker expression was examined by flow cytometry in mDCs having improved migration ability, to which the recombinant autotaxin protein has been added during culture, and mDCs to which autotaxin protein has not been added, and shown in FIGS. 12A and 12B.

As shown in FIGS. 12A and 12B, mDCs (ATX+) to which autotaxin protein has been added and mDCs (ATX−) to which autotaxin protein has not been added showed similar cell surface marker expression. Accordingly, it was confirmed that addition of autotaxin protein does not affect surface phenotype expression of DCs.

3.2 Examination of Inflammatory Cytokine Expression

To examine the effect of autotaxin protein addition on inflammatory cytokines of DCs, mDCs having improved migration ability or mDCs were co-cultured with T lymphocytes, and concentrations of inflammatory cytokines in the co-culture medium were examined by ELISA. Data were expressed as Mean±SEM (n=3).

Figure 13:
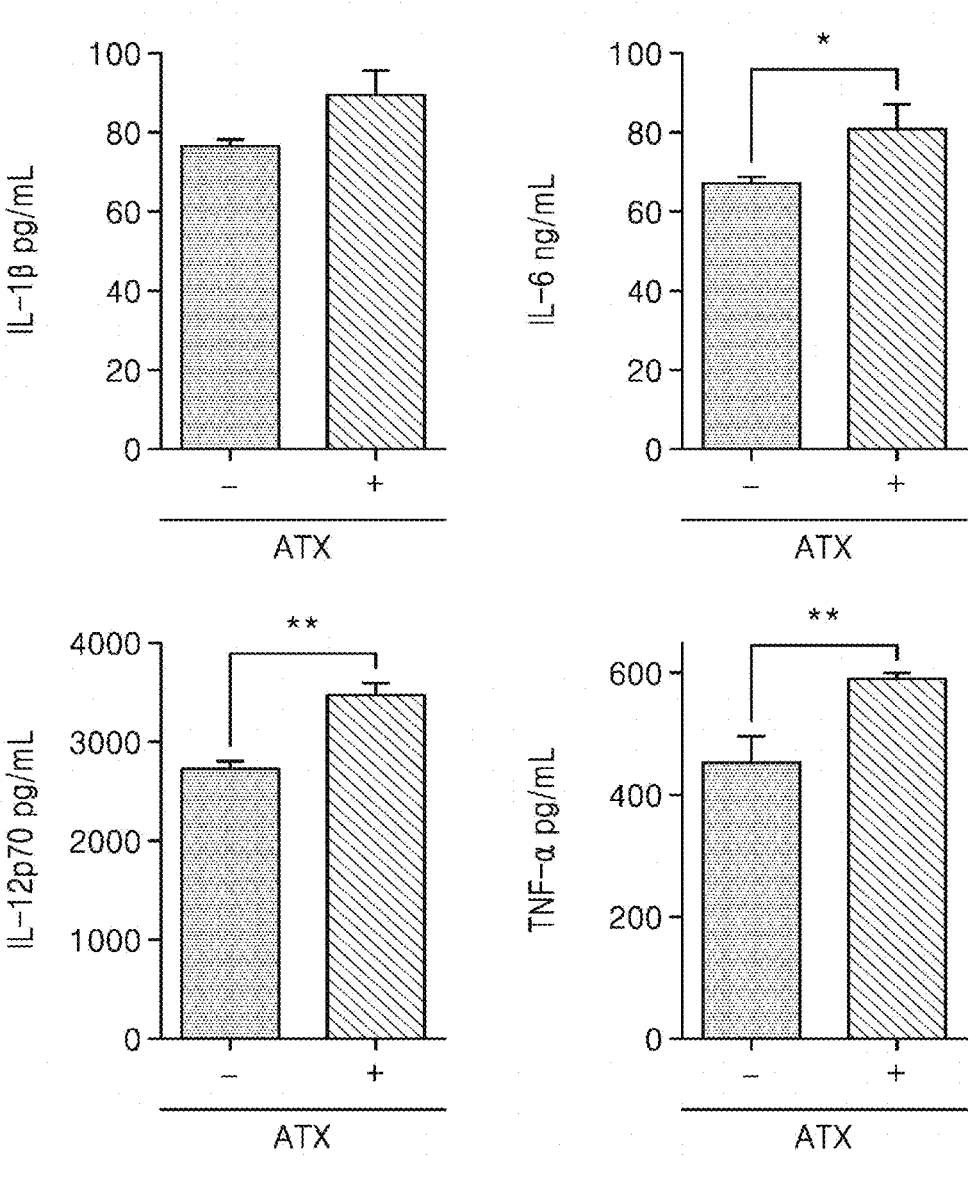
FIG. 13 shows graphs showing ELISA results of examining expression levels of inflammatory cytokines, IL-1β, IL-6, TNF-α, and IL-12p70 in mDCs (+) to which autotaxin protein has been added and mDCs (−) to which autotaxin protein has not been added (*p<0.05, **p<0.01)

FIG. 13 shows graphs showing ELISA results of examining expression levels of inflammatory cytokines, IL-1β, IL-6, TNF-α, and IL-12p70 in mDCs (+) to which autotaxin protein has been added and mDCs (−) to which autotaxin protein has not been added (*p<0.05, **p<0.01).

As shown in FIG. 13, it was confirmed that mDCs cultured with the addition of autotaxin protein produced high concentrations of inflammatory cytokines, as compared with mDCs to which autotaxin protein has not been added.

3.3 Examination of T Lymphocyte Proliferation Ability

To examine the effect of autotaxin protein addition on T lymphocyte proliferation-inducing ability of DCs, mDCs having improved migration ability or mDCs were co-cultured with CD3+ T cells at a ratio of 1:10 for 72 hr. The CD3+ T cells were isolated from splenocytes of naive C57BL/6 mouse, and stained with CFSE.

Figure 14:
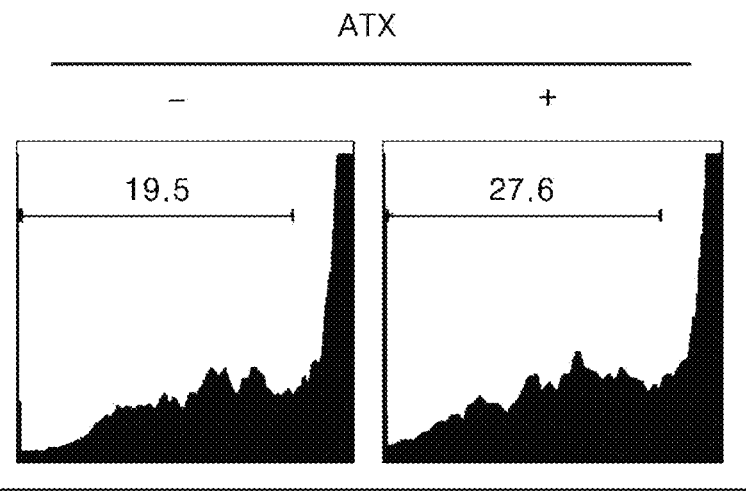
FIG. 14 shows results of examining proliferation ability of T lymphocytes in mDCs (+) to which autotaxin protein has been added and mDCs (−) to which autotaxin protein has not been added.

FIG. 14 shows results of examining proliferation ability of T lymphocytes in mDCs (+) to which autotaxin protein has been added, and mDCs (−) to which autotaxin protein has not been added.

As shown in FIG. 14, it was confirmed that mDCs cultured with the addition of autotaxin protein showed about 15% high T lymphocyte proliferation ability, as compared with mDCs to which autotaxin protein has not been added.

3.4 Examination of DC-Mediated T Cell Polarization

To examine the effect of autotaxin protein addition on DC-mediated T cell polarization, mDCs were co-cultured with CD3+ T cells at a ratio of 1:10 for 72 hr. The cells were stained with anti-CD4 and anti-IFN-γ antibodies or anti-IL-17A antibody, followed by flow cytometry.

Figure 15:
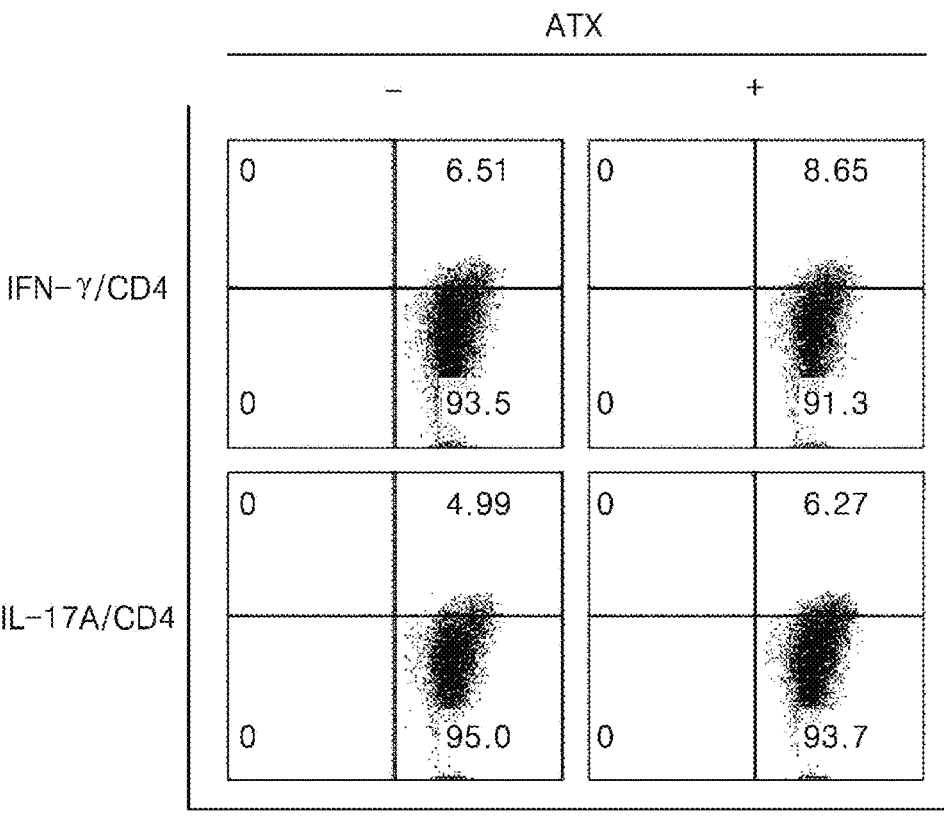
FIG. 15 shows flow cytometry results of examining IFN-γ/CD4 and IL-17/CD4 in mDCs (+) cultured with the addition of autotaxin protein and mDCs (−) cultured without addition of autotaxin protein.

FIG. 15 shows flow cytometry results of examining IFN-γ/CD4 and IL-17/CD4 in mDCs (+) cultured with the addition of autotaxin protein and mDCs (−). IFN-γ is Th1 cytokine, and IL-17 is Th17 cytokine.

As shown in FIG. 15, it was confirmed that when T cells were co-cultured with mDCs having improved migration ability cultured with the addition of autotaxin protein, they were differentiated into Th1 and Th17 subtypes about 1.5 times higher than those co-cultured with mDCs to which autotaxin protein has not been added.

Further, each of mDCs was co-cultured with CD3+ T cells at a ratio of 1:10 for 72 hr, and cell culture media were harvested, and cytokine (IFN-γ, IL-17A, IL-4, and IL-10) expression was examined by ELISA. Data were expressed as Mean±SEM (n=3).

Figure 16:
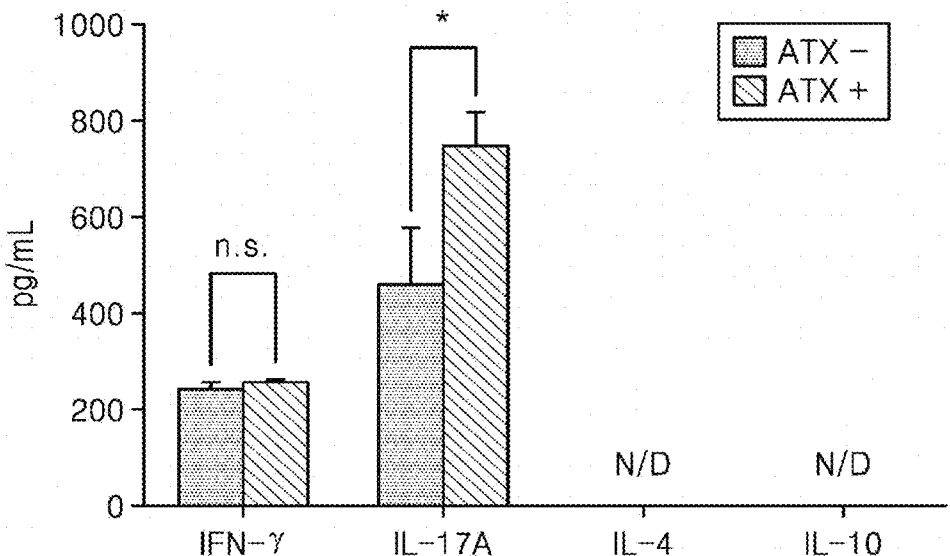
FIG. 16 shows a graph showing ELISA results of examining cytokine concentrations in a co-culture medium of mDCs (+) cultured with the addition of autotaxin protein and mDCs (−) with CD3+ T cells.

FIG. 16 shows a graph showing ELISA results of examining cytokine concentrations in the co-culture medium of mDCs (+) cultured with the addition of autotaxin protein and mDCs (−) with CD3+ T cells.

As shown in FIG. 16, high IFN-γ and IL-17 concentrations in the co-culture medium were observed in autotaxin expression-suppressed mDCs.

3.5 Examination of Rho A Protein and In Vitro Migration Ability

To examine the effect of autotaxin protein addition on a Rho A protein expression level in mDCs and migration ability of mDCs, experiments were performed in the same manner as in Examples 1.6 and 1.7.

Figure 17:
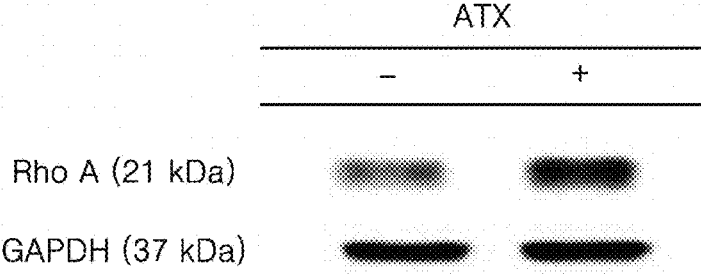
FIG. 17 shows a photograph showing ELISA results of examining RhoA protein expression in mDCs (+) cultured with the addition of autotaxin protein and mDCs (−)

FIG. 17 shows a photograph showing ELISA results of examining RhoA protein expression in mDCs (+) cultured with the addition of autotaxin protein and mDCs (−).

As shown in FIG. 17, it was confirmed that RhoA protein expression was significantly increased by about 1.5 fold or more in mDCs having improved migration ability, which were cultured with the addition of autotaxin protein.

Figure 18:
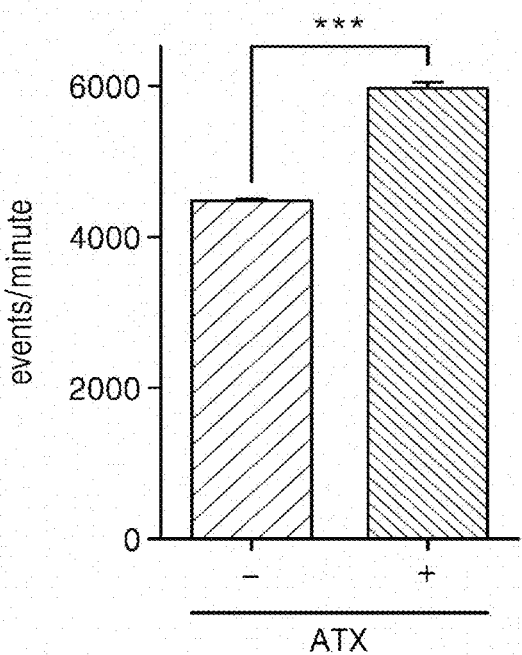
FIG. 18 shows a graph showing results of a migration assay in mDCs (+) cultured with the addition of autotaxin protein and mDCs (−) (***p<0.001)

FIG. 18 shows a graph showing results of the migration assay in mDCs (+) cultured with the addition of autotaxin protein and mDCs (−) (***p<0.001).

As shown in FIG. 18, it was confirmed that mDCs having improved migration ability, which were cultured with the addition of autotaxin protein, showed about 15% or more increased in vitro migration ability.

3.6 Examination of Intracellular Protein Expression

To examine the effect of autotaxin protein addition on intracellular signaling proteins (pp38, ERK 1/2, pJNK, NF-κB) in mDCs, expression levels of the proteins were examined by Western blotting.

Figure 19:
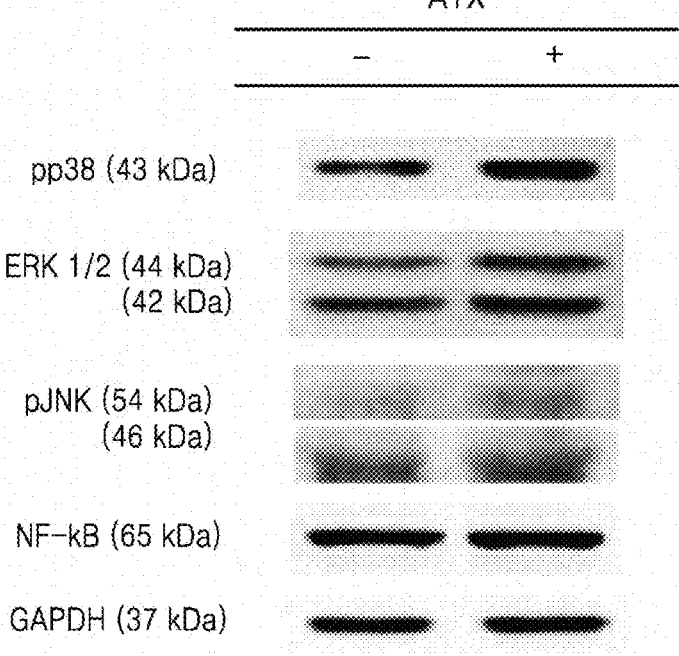
FIG. 19 shows a photograph showing Western blotting results of examining intracellular pp38, ERK 1/2, pJNK, and NF-κB protein expression levels in mDCs (+) cultured with the addition of autotaxin protein and mDCs (−)

FIG. 19 shows a photograph showing Western blotting results of examining intracellular pp38, ERK 1/2, pJNK, and NF-κB protein expression levels in mDCs (+) cultured with the addition of autotaxin protein and mDCs (−).

As shown in FIG. 19, it was confirmed that pp38, pJNK, and ERK1/2 protein expression was significantly increased in mDCs cultured with the addition of autotaxin protein.

Example 4. Evaluation of In Vivo Migration Ability of mDCs Cultured with Addition of Recombinant Autotaxin Protein During Culture To examine in vivo whether the migration ability of mDCs cultured with the addition of the recombinant autotaxin protein during culture was improved, migration of DCs was tracked.

In detail, DCs labeled with Near infrared dye (NIR) using a CellVue® NIR815 Midi Kit for Membrane Labeling (Polysciences Inc., Warrington, UK) were suspended in PBS, and then $1 \times 10^5$ cells/50 μL were subcutaneously injected into the paw pad of C57BL/6 mouse. At 24 hour intervals immediately after injection, DC migration was tracked using Pearl Impulse (LI-COR biotechnology, NE, USA) equipment for 72 hr. Imaging was performed using a near-infrared 800-nm channel emitted at a wavelength of 778 nm and detected at 794 nm. An image on the $3^{rd}$ day after injection was used as a representative image.

Figure 20:
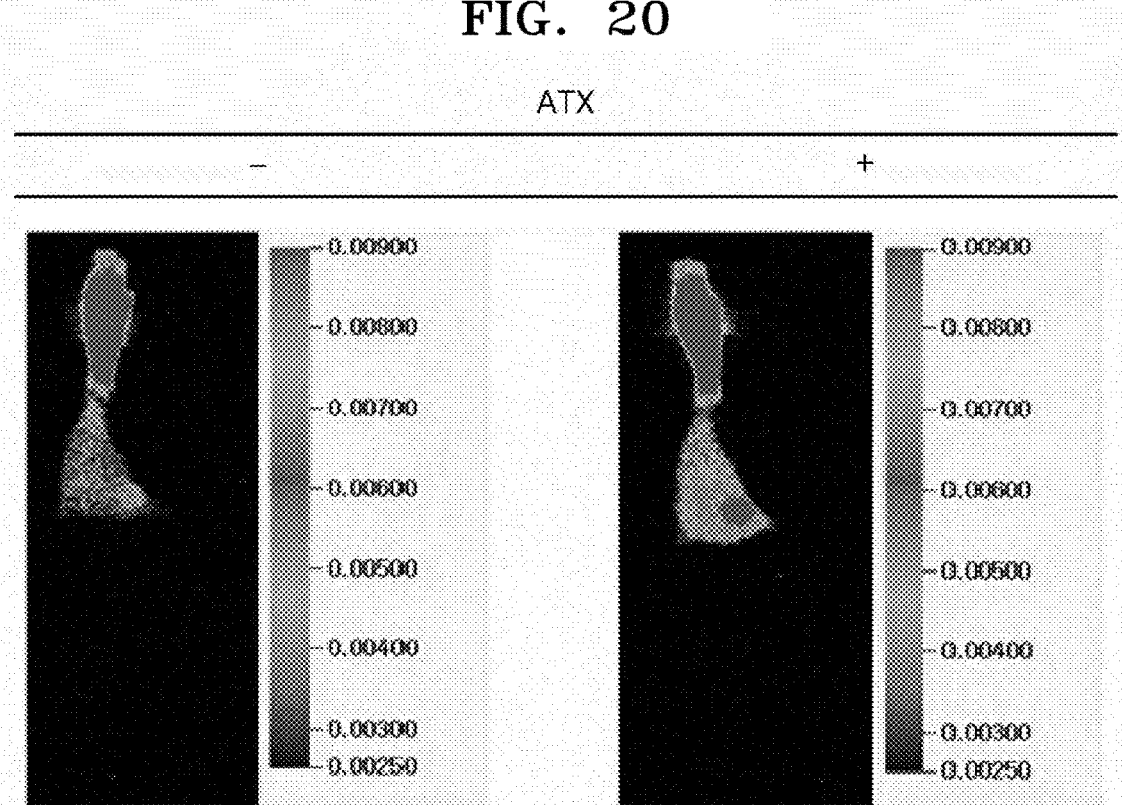
FIG. 20 shows a photograph showing a trace of migration to popliteal lymph nodes by mDCs (+) cultured with the addition of autotaxin protein and mDCs (−), over 3 days.

FIG. 20 shows a photograph showing a trace of migration to popliteal lymph nodes by mDCs (+) cultured with the addition of autotaxin protein and mDCs (−), over 3 days.

As shown in FIG. 20, mDCs cultured with the addition of autotaxin protein showed 4 times higher migration to popliteal lymph node on average, as compared with mDCs cultured without the addition of autotaxin protein.

Accordingly, it was confirmed that migration ability of mDCs was improved by addition of autotaxin protein during culture.

Figure 21:
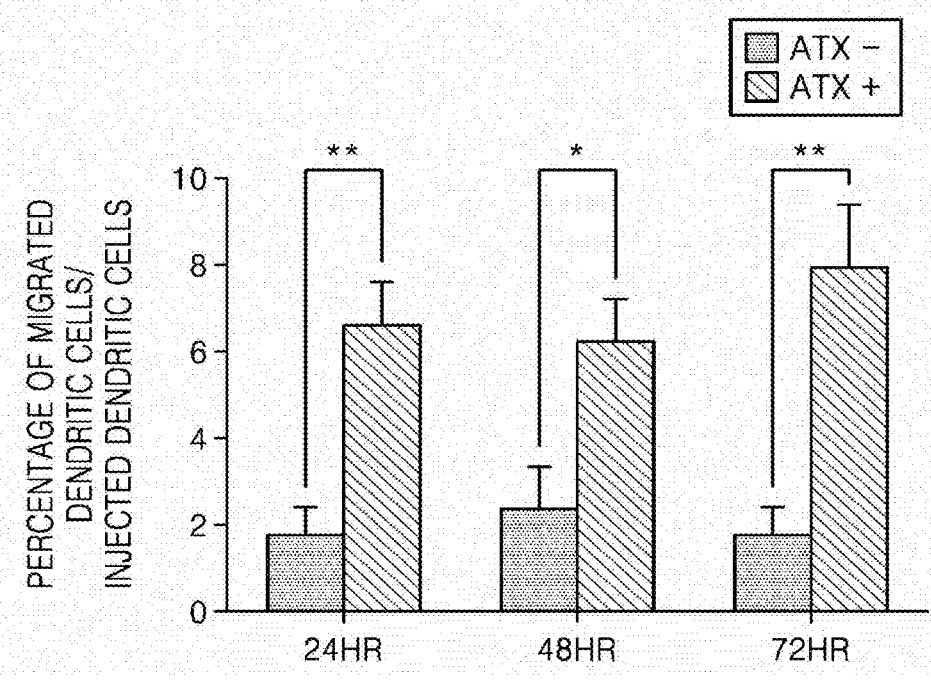
FIG. 21 shows a graph showing quantification of the proportion of mDCs (+) cultured with the addition of autotaxin protein and mDCs (−) that migrated to popliteal lymph nodes over 3 days.

Further, after converting the total fluorescence intensity detected in the mouse to 100%, the migration efficiency was quantified, relative to the fluorescence values of those that migrated to the popliteal lymph node, and the results are shown in FIG. 21 (*p<0.05, **p<0.01).

As shown in FIG. 21, the proportion of the DC line that migrated to the lymph node to the injected DC line was significantly increased over time.

Further, to examine the proportion of the DCs that migrated to the mouse popliteal lymph node by confocal microscopy, carboxyfluorescein succinimidyl ester (CFSE) (Molecular Probes, OR, USA) fluorescence-labeled dendritic cells were injected into a mouse in the same manner as above, and 24 hr later, popliteal lymph nodes were removed. The removed popliteal lymph nodes were fixed with 4% paraformaldehyde, and frozen sections were prepared. The tissue section which was cut to a thickness of 10 μm was attached to a slide and treated with a DAPI mounting solution (Immunobioscience Co., WA, USA), and then images were obtained using Zeiss LSM 510 (Carl Zeiss Co., Oberkochen, Germany). Images were analyzed using a Zeiss ZEN software (Carl Zeiss). Results are shown in FIG. 22.

Figure 22:
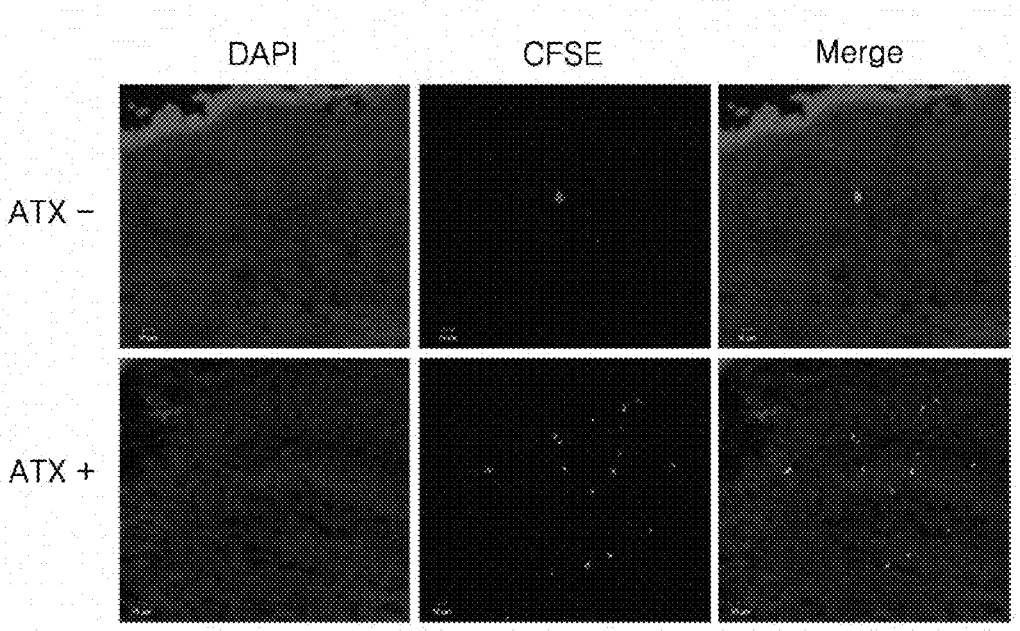
FIG. 22 shows confocal microscopy results of analyzing the proportion of mDCs (+) cultured with the addition of autotaxin protein and mDCs (−) that migrated to popliteal lymph nodes over 3 days.

As shown in FIG. 22, it was confirmed that mice injected with mDCs (+) cultured with the addition of autotaxin protein showed high migration of the cells to the popliteal lymph node, as compared with the control group injected with mDCs (−).

Further, lymphocytes were isolated from the removed popliteal lymph node, and stained with anti-CD11c antibody, followed by flow cytometry. Results are shown in FIG. 23.

Figure 23:
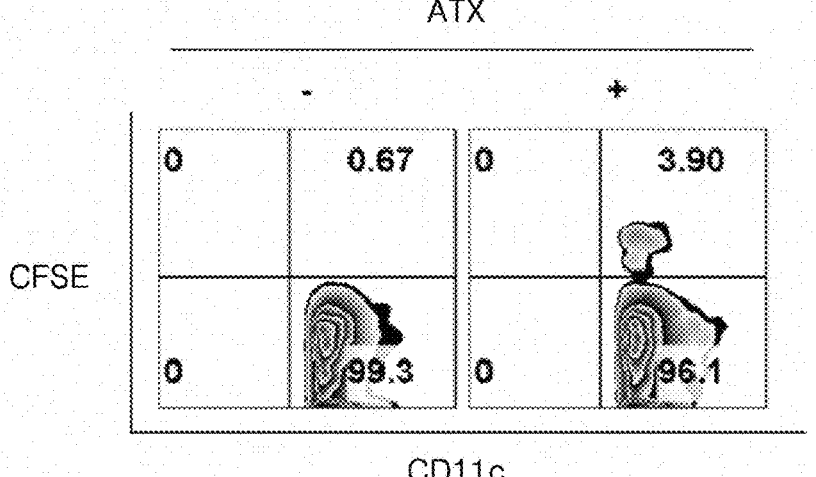
FIG. 23 shows flow cytometry results of examining mDCs after separating lymphocytes from removed popliteal lymph nodes and staining the lymphocytes with CD11c antibody.

As shown in FIG. 23, it was confirmed that the proportion of CFSE+ and CD11c+ DCs in the popliteal lymph node of the mice injected with mDCs (+) cultured with the addition of autotaxin protein was 5 times higher than that in the control group.

Accordingly, it was confirmed that when cultured with the addition of autotaxin protein, the migration ability of mDCs is improved.

Statistical Analysis

The experimental results of this study were tested for statistical significance by Student's t-test method for at least 3 repeated experiments. Statistical significance was expressed as follows: *p<0.05, p<0.01, *p<0.001.

The invention claimed is:

1. A method of preparing mature dendritic cells having increased migration ability, the method comprising:

culturing isolated immature dendritic cells with (i) an RPMI medium comprising fetal bovine serum (FBS), granulocyte-macrophage colony-stimulating factor (GM-CSF), interleukin-4 (IL-4), and mercaptoethanol, and (ii) additives comprising a recombinant autotaxin, lipopolysaccharide (LPS), and keyhole limpet hemocyanin (KLH), wherein the recombinant autotaxin is in an amount sufficient to increase mature dendritic cells motility compared to mature dendritic cells prepared by culturing isolated immature dendritic cells with the RPMI medium comprising FBS, GM-CSF, IL-4, and mercaptoethanol, and additives comprising the LPS and KLH, but without recombinant autotaxin.

2. The method of claim 1, wherein the immature dendritic cells are immature dendritic cells, semi-mature dendritic cells, or a combination thereof.

3. The method of claim 1, wherein the immature dendritic cells are obtained by culturing bone marrow cells from which red blood cells were removed.

4. The method of claim 1, wherein the method increases induction of inflammatory cytokine production, induction of T lymphocyte proliferation, or induction of T lymphocyte polarization of dendritic cells.

\* \* \* \* \*